United States Patent [19]
Stahmann et al.

[11] Patent Number: 5,376,106
[45] Date of Patent: Dec. 27, 1994

[54] MULTI-SENSOR BLENDING IN A RATE RESPONSIVE CARDIAC PACEMAKER

[75] Inventors: Jeffrey E. Stahmann, Ramsey; Jesse W. Hartley, Shoreview, both of Minn.

[73] Assignee: Cardiac Pacemakers, Inc., St. Paul, Minn.

[21] Appl. No.: 136,892

[22] Filed: Oct. 18, 1993

[51] Int. Cl.$^5$ .............................................. A61N 1/365
[52] U.S. Cl. ....................................................... 607/18
[58] Field of Search ..................................... 607/17, 18

[56] References Cited

U.S. PATENT DOCUMENTS

| | | |
|---|---|---|
| 4,688,573 | 8/1987 | Alt . |
| 4,782,836 | 11/1988 | Alt . |
| 4,867,161 | 9/1989 | Schaldach . |
| 5,063,927 | 11/1991 | Webb et al. . |
| 5,065,759 | 11/1991 | Begemann et al. . |
| 5,097,831 | 3/1992 | Lekholm .................. 607/18 |

*Primary Examiner*—William E. Kamm
*Attorney, Agent, or Firm*—Haugen and Nikolai

[57] ABSTRACT

A multi-sensor blending circuit for use in a rate responsive cardiac pacemaker. The blending logic circuit blends delta pacing rate signals from two or more sensors which measure physical and physiological parameters of a patient. Programmable equations stored in the blending logic circuit determine which percentages or a ratio of the delta pacing rate sensor signals comprise a single delta pacing rate signal as a function of the delta pacing rate. This delta pacing rate signal is provided to the pacing control circuitry of a pacemaker. The blending ratios are dynamically determined based on the pacing rate established at the most recent cardiac cycle. The blending equations are comprised of several programmable variables, wherein the equations can be programmed by the external programmer in view of clinical data.

8 Claims, 4 Drawing Sheets

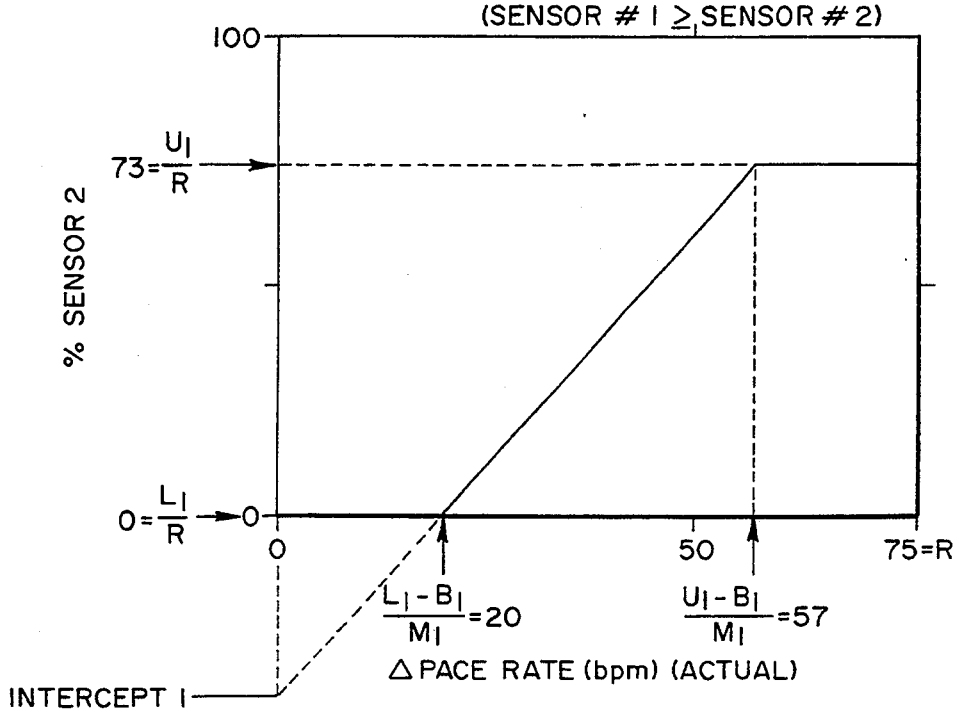
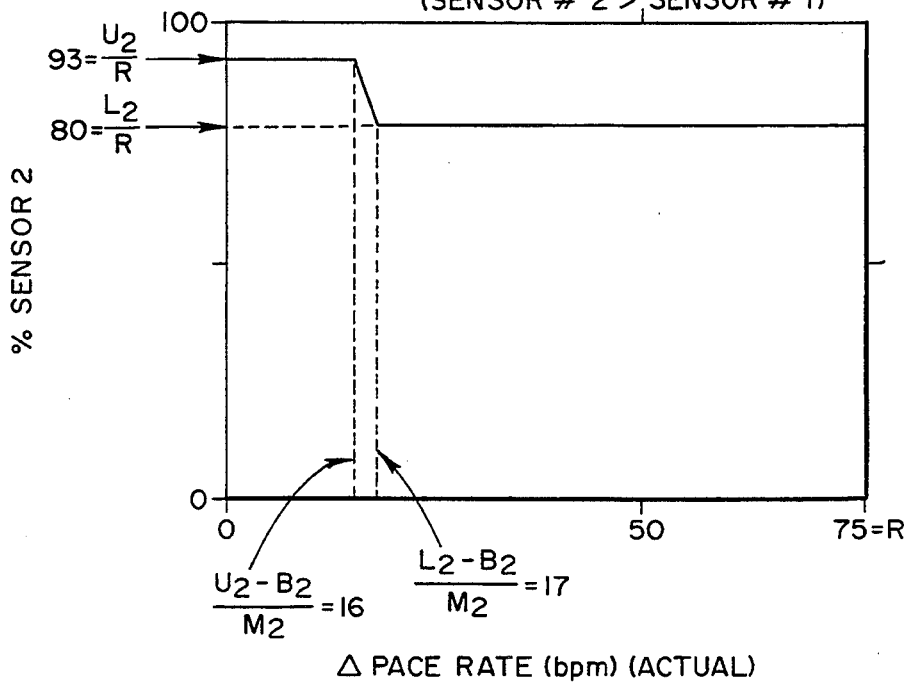

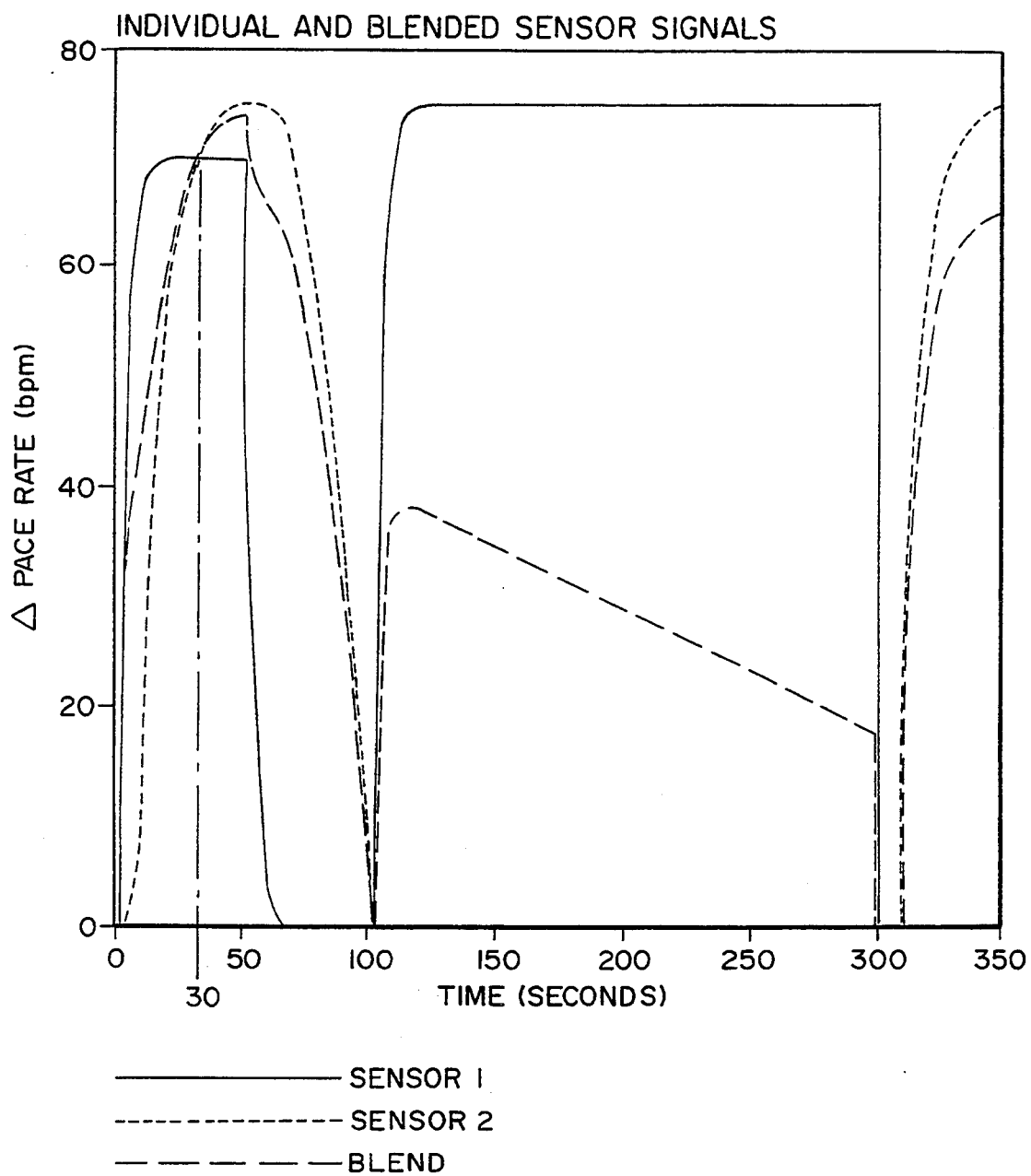

MULTI-SENSOR BLENDING IN A RATE RESPONSIVE CARDIAC PACEMAKER

FIELD OF THE INVENTION

This invention relates generally to rate responsive cardiac pacemakers, and more particularly, to implantable cardiac pacemakers with blending logic circuits for determining a delta pacing rate based upon signals from a plurality of sensors, including both physiological sensors and sensors indicating physical activity.

BACKGROUND OF THE INVENTION

Rate-responsive or demand-type cardiac pacemakers are widely available in the industry. In contrast to programmable fixed rate pacemakers, rate responsive pacemakers implement one or more sensors for monitoring and indicating various attributes of a patient, including both a patient's physiological needs, as well as detected physical activity levels. Various devices and algorithms are known in the art for determining the outputs from sensors and controlling the pacing rate as a function of the sensor outputs. These various prior art devices attempt to account for time delays when sensing attributes of a patient's need, and for false or inaccurate sensor outputs, such as the output provided by an accelerometer when the patient travels over a rough road in an automobile.

Many parameters can be continuously sensed and responded to by the pacemaker via the sensors when determining the optimal pacing rate, given the conditions of the patient as sensed by the sensors. Such parameters include sensing the QT interval, which is the time interval between a delivered pacing stimulus and the subsequent evoked T-wave. Activity sensors such as accelerometers, as well as sensors for obtaining a patient's respiration rate, thoracic impedance changes, venous blood temperature, PH levels, oxygen saturation, and heart stroke volume are all known in the prior art for use with pacing circuitry.

Generally, no one parameter is adequate standing alone as a basis for determining a delta pacing rate of a rate responsive pacemaker. Delta pacing rate is defined as the increased pacing rate above a predetermined minimum pacing rate. While each sensed parameter is helpful for ascertaining a patient's present condition when determining the optimal pacing rate, prior art devices have recognized the advantage of sensing more than one parameter when determining the optimal pacing rate. One approach is to use a first sensor to qualify a second sensor. The pacing rate is thus based on one sensor as long as the second sensor "qualifies" the rate increase as legitimate. This greatly reduces the potential benefits of a two sensor pacemaker since for the majority of the time the pacing rate is based only on one sensor. A second approach blends the two sensors at a constant percentage, such as 50%. This method simply dilutes the input of one sensor with the other and thereby reduces the worst and the best characteristics of each sensor.

Other methods of combining sensor inputs within a pacemaker are non-programmable, or at the very best, rigid and allow no fundamental changes in the method by which the sensors are combined. This makes adaption of clinical investigations leading to improved blending algorithms much more difficult. In addition, patients having pacing devices using old blending algorithms cannot take advantage of improved blending algorithms without replacement of their present pacemaker.

U.S. Pat. Nos. 4,688,573 and 4,782,836 to Alt teach a rate adaptive cardiac pacemaker responsive to patient activity and temperature. This invention teaches using two different algorithms, one exclusive of the other, depending on whether the output of a temperature sensor has exceeded a predetermined temperature threshold. The two algorithms are characterized as an exercise algorithm, and an algorithm for patient inactivity. The primary sensor is an activity sensor such as a piezoelectric crystal for detecting movement of the patient.

U.S. Pat. No. 5,065,759 to Begemann et al. teaches a pacemaker with optimized rate responsiveness and method of rate control. The algorithm taught is based upon implementing two sensors, one designated as having a fast sensor rate, and the other designated as having a slow sensing rate. One sensor provides a parameter taken as the primary control parameter, and the other provides a parameter which is converted into corresponding units so as to be comparable for control purposes. An algorithm compares the difference between the detected sensing rates, and determines an adjust rate difference (drift). The pacing rate is established by incrementing the pacing rate at a rate depending upon this drift rate and a predetermined factor "C". Thus, gradual rate changes are achieved through incremental adjustments, and are based on inputs alone and without using feedback. This device implements two sensors, wherein one may remain deactivated until a sufficient magnitude indicating the undertaking of physical exertion. Upon activation of the first sensor, a linear increase in the pacing rate is performed at a predetermined rate but which is not to exceed a predetermined upper threshold. Similarly, when the activity sensor senses a reduction of physical activity, the pacing rate will fall progressively but not below a minimum rate. Thus, one sensor serves to determine whether a pacing rate should be increased or decreased, and the other sensor serves to modify the upper and lower pacing limits. In effect, the second sensor serves to modulate the upper limits.

U.S. Pat. No. 5,063,927 to Webb teaches a rate responsive pacemaker which generates a pacing signal as a function of two separate sensors. If a change of a pacing is to be performed, the delta pacing rate is a predetermined and fixed increase or decrease, such as one beat/minute/second, and the delta pacing rate is not variable or dependent on variables.

U.S. Pat. No. 4,867,161 to Schaldach teaches a cardiac pacemaker implementing matrix logic for determining a pacing rate. The matrix provides a look-up table based strictly on inputs from sensors when determining a delta pacing rate, and doesn't implement feedback such as using a current pacing rate as an input variable to the matrix. Thus, transitions between a fast pacing rate and a slow pacing rate are not necessarily smooth, and may be noticed by the patient.

Accordingly, an improved rate responsive pacemaker having two or more sensors for sensing parameters of a patient is desired which simultaneously uses and blends the sensed parameters when establishing the optimum pacing rate. An algorithm which provides for a smooth transition when altering a pacing rate by utilizing the pacing rate established by previous pacing pulses is desired. To utilize the benefits of each sensor, one should not be excluded from the other except when a sensor output is deemed invalid.

OBJECTS

It is accordingly an object of the present invention to provide a rate responsive pacemaker including logic for blending two or more sensor inputs simultaneously when determining a pacing rate.

It is accordingly a further object of the present invention to provide a rate responsive pacemaker wherein the blending algorithm can be fixed, or selectively programmed by a physician either at time of implantation or external to the body after implantation.

Still yet a further object of the present invention is to provide a rate responsive pacemaker which utilizes the sensor inputs in a variety of ways depending on the sensed parameters, and further which implements feedback to achieve a smooth transition of pacing rates.

Other objects, features and advantages of the present invention will become apparent to those skilled in the art through the Description of the Preferred Embodiment, Claims, and drawings herein, wherein like numerals in the various figures refer to like elements.

SUMMARY OF THE INVENTION

The foregoing objects and advantages are achieved by providing a rate responsive cardiac pacemaker having a blending logic circuit including feedback for arbitrating and/or mixing two or more sensor outputs and using a percentage of each to determine a single delta pacing rate as a function of the actual or current pace rate. More specifically, the pacemaker includes a first and second sensor for sensing attributes of a patient's body and generating a first and second output, respectively, each directly or indirectly indicative of a delta pace rate. A delta pace rate is defined as the difference between the pace rate and a predetermined minimum pacing rate. The blending logic circuit is coupled to the first and second sensors for arbitrating and/or combining the first and second outputs to generate a single blended output signal as a function of the delta pace rate serving as feedback and which closes the loop. The blended output signal is comprised of a first percentage of the first sensor output, and a second percentage of the second sensor output. A processor is coupled to the blending logic circuit for producing a pacing signal at a pacing rate determined as a function of the blended output signal. A pacing mechanism is coupled to the processor for pacing the patient's heart as a function of the pacing signal at the pacing rate.

In a preferred embodiment of the present invention, the first and second percentages of the blending logic circuit are variably defined by an equation stored in the blending logic circuit. This equation determines the variable first and second percentages as a function of the delta pacing rate and sensor inputs, which again, the delta pacing rate is defined as the increased pacing rate above a minimum predetermined pacing rate. Further, the pacemaker preferably includes programming circuitry thus allowing a physician to selectively program the equation parameters in the blending logic circuit. A receiver is provided in the pacemaker for receiving and relaying programming signals generated external of the pacemaker. The programming circuitry is responsive to the relayed programming signals for programming the equation parameters in the blending logic circuit. Thus, the physician can reprogram the parameters of the equation in the blending circuit means when desired, such as to take advantage of improved blending algorithms determined through clinical investigations without replacement of the present pacemaker.

Preferably, the equation programmed in the blending logic circuit is characterized in that the first and second percentages are defined as a function of the first sensor output in relation to the second sensor output. Specifically, the first and second percentages are established dependent upon whether the first output signal is greater than, equal to, or less than the second sensor output signal. Preferably, the equation is at least of a second order mathematical equation. The present invention further includes an evaluating circuit coupled to the blending logic circuit for conditioning one or more of the sensor outputs and attenuating the respective sensor outputs when generating the blended output signal.

BRIEF DESCRIPTION OF THE DRAWINGS

FIG. 3A illustrates what portion of the blended output signal is comprised of the second sensor output as a function of the delta pacing rate when the delta pacing rate of the first sensor is greater than the delta pacing rate of the second sensor;

FIG. 3B also illustrates what percentage of the blended output signal is comprised of the second sensor output, as a function of the delta rate when the delta pacing rate indicated by the second sensor is greater than the delta pacing rate indicated by the first sensor; and FIG. 4 is a graphical illustration of both individual and blended sensor signals, wherein the individual sensor signals from the first and second sensors are inputted to the blending logic circuit, and the blended sensor signal is the output which is provided to the pacer control logic circuit and is determined by the equation stored in the blending logic circuit.

DESCRIPTION OF THE PREFERRED EMBODIMENT

Figure 1:
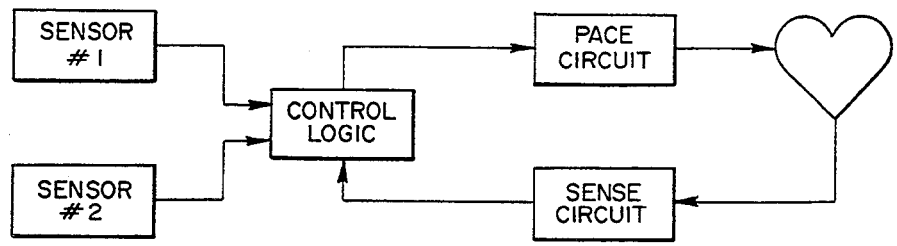
FIG. 1 illustrates a typical prior art pacemaker including control logic circuitry establishing a pace rate and a delta pace rate as a function of only inputs from sensors, and without feedback.

Referring now to FIG. 1, a block diagram of a typical prior art rate responsive pacemaker is shown. A discrete circuit or microprocessor based control logic circuit is responsively coupled to two or more patient sensors, and interfaces with both a pacing circuit and a sensing circuit to properly control pacing of the heart as a function of the sensor inputs. Typical parameters of the patient sensed by the sensors include activity measured by an accelerometer, a patient's temperature using a thermistor in a lead or a temperature sensor positioned within the pacemaker can, blood pressure sensors and PH sensors which can be disposed on one of the pacemaker leads, and sensors which can measure minute ventilation. These sensors and their application are well known in the art.

Prior art control logic responsively processes the input signals indicative of the sensed parameters in a variety of ways. In some prior art pacemakers, the control logic uses one sensor input signal to qualify the second sensor input signal. The pacing rate established by the control logic and communicates to the pacing circuit is based only on one sensor so long as the second sensor "qualifies" a delta pacing rate increase as legitimate. This greatly reduces the potential benefits of a two sensor pacemaker since for the majority of the time the pacing rate is based only on one sensor. Other prior art algorithms simply blend the outputs from the two sensors at a constant percentage, wherein this method "dilutes" the input of one sensor with the input from the other and thus reduces the worst and the best characteristics of each sensor. None of the prior art approaches teach an rate adaptive blending logic circuit which dynamically establishes ratios of the inputs from both sensors as a function of the pacing rate or the delta pacing rate, which delta pacing rate is provided as feedback and is defined as the difference between the pacing rate and a predetermined minimum pacing rate.

Figure 2:
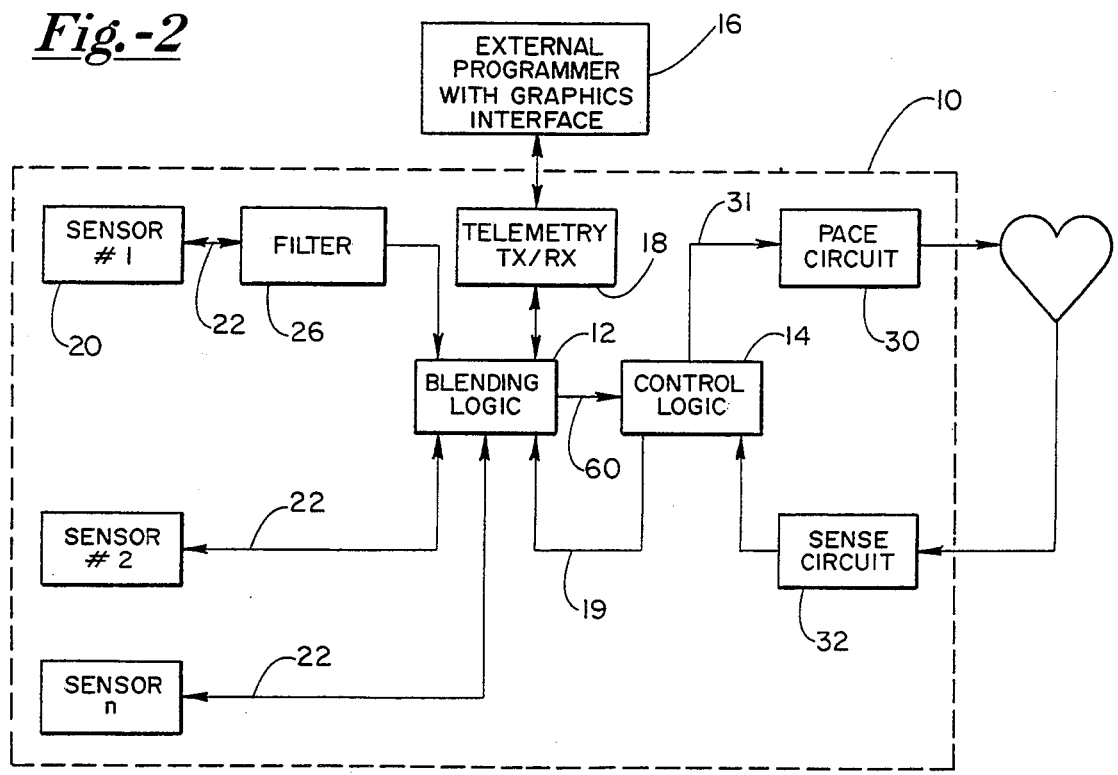
FIG. 2 is a block diagram of a rate responsive pacemaker including feedback with a blending logic circuit for arbitrating and/or mixing output signals from a pair of sensors as a function of the delta pacing rate, wherein the blended or mixed signals are provided as a single input to a pacing control logic circuit.

Referring now to FIG. 2, a block diagram of a pacemaker according to the preferred embodiment of the invention is shown at 10 including a blending logic circuit 12 which arbitrates and/or combines delta pacing rate signals from two or more sensors, which sensors provide physical and physiological parameters of the patient. Blending logic circuit 12 mixes or blends the delta pacing rate signals from each of the sensors based on a predetermined, but preferably variable ratio. This ratio defines the percentage or portion of each of the sensor signals which comprise a single delta pacing rate signal provided by the blending logic circuit 12 to control logic circuit 14. Control logic 14 determines a pacing rate as a function of the single delta pacing rate signal and instructs pacing circuitry 30 via line 31 to pace the heart at the pacing rate.

The variable ratio and predetermined percentages are determined by at least one logic equation stored in a memory of blending logic 12. Each of the blending logic equations has several parameters which are determined and defined by the physician at time of implantation, or are defined by an external programmer 16 via transmitter/receiver telemetry 18. As the value of the delta pacing rate provided by the control logic 14 via line 19 changes, the percentages of each of these delta rate signals implemented to form the single delta pacing signal dynamically changes as well. The feedback of the delta pace rate signal closes the loop and is provided from control logic circuit 14 to blending logic 12 via line 19, which delta pace rate forms a subset of the pace rate comprising of a predetermined base rate and the delta pace rate. Thus, in effect, the blending ratio inherently changes as a function of the pacing rate.

A plurality of sensors 20, comprised of any well known physical and physiological sensors typically implemented in rate responsive pacemakers, form a portion of pacemaker circuit 10. For instance, accelerometers for measuring physical movement, impedance sensors employed to sense minute ventilation, temperature sensors, blood pressure sensors, and PH sensors all can be employed in the present invention. Each of these sensors include some form of signal processing, such as sample averaging, such that upon sensing the respective physical or physiological parameter, the signal output from the respective sensor is indicative of a delta pacing rate. The signals outputted from each of sensors 20 are provided on respective output lines 22, and are provided in either a digital or analog format. In the preferred embodiment, all signal processing is done digitally, however, limitation to a digital implementation is not to be inferred.

Pacemaker circuitry 10 also includes a filter 26 inserted between sensor number 1 and the blending logic circuit 12 to alternate suspect signals, such as prolonged signals from an accelerometer as the patient traverses over a rough road in a car, before the outputted signal is applied to the equations in blending logic circuit 12. While filter 26 is shown interposed between one sensor 20 and blending logic 12, it is recognized in the art that an appropriate filter 26 could be implemented for one or more sensor, and defined integral to the respective sensor 20 itself, or implemented in the blending logic circuit 12, and limitation to a discrete filter interposed therebetween is not to be inferred. For instance, when processing the sensor signals in the digital implementation, filter 26 will unilaterally condition the respective signal before it is communicated to blending logic circuit 12 and there applied to the equations. If, for instance, analog signal processing techniques are implemented, a high pass filter can be used to reduce the signal level before it is communicated to blending logic circuit 12. Thus, when one of the sensor inputs is accelerometer based and the other is not, such as minute ventilation, temperature, cardiac impedance, etc., the present invention provides a method for limiting consideration of the rate increase from sensor number one due to misleading physical motion over time.

The equations of the present invention can be programmed such that only a single sensor is normally operating and the remaining sensor is inactive. This feature allows reduction of the overall power requirements of the pacemaker to extend the useful life of a pacemaker battery. If such a feature is programmed into the equations, the sensor can be selectively implemented by blending logic 12 via line 22 only when a particular delta pace rate increase is provided by the other. For instance, if sensor number two is a physiological sensor, the equations in blending logic 12 can be programmed to not recognize the signal from sensor number one, which may comprise of an accelerometer, until the delta pacing rate from sensor number 2 exceeds a predetermined minimum threshold. Of course, this qualifying principle can be applied to a pacing device incorporating more than two sensors.

One of the principle features of blending logic circuit 12 is that the blending parameters of the equations can be reprogrammed via telemetry using, for example, RF or ultrasonic signals transmitted between external programmer 16 and blending logic circuit 12 via telemetry transmitter/receiver 18. Thus, this invention provides a method for altering the parameters of the blending equations based on clinical data gathered. Further, clinical data could be evaluated by programming the equation parameters with values based on new theories wherein the patient would then be subsequently monitored. This flexibility also enables the device to be programmed to match the individual requirements of a much greater patient population. As mentioned earlier, control logic 14, pace circuit 30 and sensing circuit 32 are well known in the art. The present invention including the novel blending logic and blending circuit 12 is ideally adapted to be interposed between the sensors 20 and control logic circuit 14.

To illustrate the operation and features of the present invention by way of example, a typical programming set up of the equations in blending logic circuit 12 will now be discussed, and then will be applied to a variety of scenarios or combinations of different delta pacing rate signals from the sensors.

A preferred blending formula used in the preferred embodiment in the invention for determining a single delta pacing rate for control logic circuit 14 is as follows. The first rate equation is implemented by blending logic 12 when the delta pacing rate signal from sensor one is greater than the delta pacing rate signal from sensor two, and wherein the second equation is implemented when the delta pacing rate from sensor number two is greater than the delta pacing rate signal from sensor one:

EQUATION 1

$$\text{delta rate} = [B_1(s_2-s_1)+s_1R]/[R-M_1(s_2-s_1)] \quad s_1 \text{ greater than } s_2$$

EQUATION 2

$$\text{delta rate} = [B_2(s_2-s_1)+s_1R]/[R-M_2(s_2-s_1)] \quad s_2 \text{ greater than } s_1$$

where
R = maximum sensor rate − lower rate limit
$B_1$ = Rate intercept when $s_1$ greater than $s_2$
$B_2$ = Rate intercept when $s_2$ greater than $s_1$
$M_1$ = Slope when $s_1$ greater than $s_2$
$M_2$ = Slope when $s_2$ greater than $s_1$ The rate specified by these equations is the delta pacing rate due to the sensor inputs. The lower rate limit must be added to this delta rate to get the actual pacing rate, which actual pacing rate is established by control logic circuit 14.

These formulae define a linear relationship (i.e. line) between the delta pacing rates from the sensors 20 and the blending ratio. Programming of these lines will define many different blending options. Four additional constants are used to give additional flexibility to the blending lines defined above. These constants allow two zero-slope segments on both ends of the lines defined by the constants shown above. These segments can be used to add features such as:

Maximum dependents on any one sensor;
Shutting off one sensor until a certain rate is achieved;
Rapid transitioning between sensors;
Different maximum and/or minimum pacing rates for each sensor.

The four additional constants are:
$L_1$ = Lower clip when $s_1$ greater than $s_2$;
$L_2$ = Lower clip when $s_2$ greater than $s_1$;
$U_1$ = Upper clip when $s_1$ greater than $s_2$;
$U_2$ = Upper clip when $s_2$ greater than $s_1$ In the preferred embodiment of the invention, the following variable values are as follows:

| PARAMETER | LEGEND SYMBOL | VALUE |
|---|---|---|
| Range | R | 75 bpm |
| Intercept 1 | B1 | −30 bpm |
| Intercept 2 | B2 | 200 bpm |
| Slope 1 | M1 | 1.5 |
| Slope 2 | M2 | −8 |
| Lower Clip 1 | L1 | 0 bpm |
| Lower Clip 2 | L2 | 60 bpm |
| Upper Clip 1 | U1 | 55 bpm |
| Lower Clip 2 | U2 | 70 bpm |

These two blending equations using the above parameter values are graphically represented for illustration purposes in FIGS. 3A and 3B, respectively. FIGS. 3A and 3B show graphical representations of the first and second rate equations above, however, limitation to these particular curves and the selected values for the parameters which define these curves is not to be inferred, and the following graphs and parameter values are provided by way of illustration.

FIG. 3A illustrates the contributing percentage of a delta pacing rate provided by sensor 2 used to define the blended output as a function of the delta pacing rate established by the most recent pace pulse (provided by control logic 14) when the value of the delta pacing rate provided by sensor number 1 is greater than or equal to a delta pacing rate provided by sensor number 2 ($s_1 \geq s_2$). Thus, sensor number 1 is the dominant sensor in this figure. The contributing percentage of the delta pulse rate of sensor number 1 used to define the blended rate is the difference from 100%. FIG. 3B is a graphical illustration of the second equation when sensor number 2 is the dominant sensor, i.e., when the delta pacing rate of sensor number 2 is greater than the delta pacing rate provided by sensor number 1 ($S_2 > S_1$). In this figure, the percentage of the delta pacing rate provided by sensor number 2, as shown, is also as a function of the pacing rate established by the most recent pace pulse. Similarly, the contributing percentage of the delta pace rate of sensor number 1 to define the blended delta pace rate is the difference of sensor number 2 from 100%.

In regards to FIG. 3A, it can be seen that the contributing percentage of the signal from sensor number 2 forming the single blended delta pacing rate remains at zero ($L_1/R=0$) until the delta pacing rate of exceeds 20 ($L_1-B_1/M_1=20$) beats per minute (bpm). From 20 to 57 ($U_1-B_1/M_1=56.6$) beats per minute the contributing percentage of the signal from sensor number 2 linearally increases until a maximum of 73% ($U_1/R=0.73$) of sensor number 2 will be used for the outputted delta pacing rate from blending logic circuit 12. Hence, 27% of the delta pacing rate from sensor number 1 will be used. Delta pacing rates from control logic 14 which exceed 57 realize the same ratio, namely, using 73% of sensor number 2's rate and 27% of the delta pacing rate provided by sensor number 1 (73+27=100%).

Referring to the graph shown in FIG. 3B, which graphically illustrates equation number 2 and is implemented when the delta pacing rate of sensor number 2 is greater than the delta pacing rate of sensor number 1, the following can be observed. While the delta pacing rate established by control logic 14 is between 17 ($L_2-B_2/M_2=17.5$) and 75 ($R=75$) beats per minute, 80% ($L_2/R=0.80$) of the delta pacing rate sensor number 2 is used to define the delta pacing rate signal outputted from blending logic circuit 12. Thus, only 20% (80+20=100%) of the delta pacing rate from sensor number 1 forms the single delta pacing rate outputted from blending logic 12.

As the delta pacing rate drops from seventeen to sixteen ($U_2 - B_2/M_2 = 16.25$) beats per minute, the blending ratio quickly but smoothly changes to 7% sensor number 1, and 93 ($U_2/R = 0.93$) percent sensor number 2. (7+93=100%). This is an example of rapid transitioning between two blending ratios. Also noted is that by keeping the blending rate based mostly from sensor number 2, the effect of the rapid decay of the percentage of sensor number 1 used is greatly reduced. This is a very desirable feature if sensor number 1 decays too quickly, for instance, if the signal is produced by an accelerometer.

In summary, FIGS. 3A and 3B graphically illustrate the percentage of the delta pacing signal used from sensor 2 as a function of the delta pacing rate of the previous iteration, which is provided as feedback, to form a single delta pacing rate signal for control logic 14. These graphs are the graphical representations of equations 1 and 2, respectively, wherein the parameters have the values defined above.

Referring now to FIG. 4, the application of equations one and two graphically shown in FIGS. 3 and 3B is shown, wherein the delta pacing rate signals from sensors number 1 and 2 are concurrently shown with the final blended delta pacing rate signal derived from equations one or two. Whether the delta pacing rate from sensor number 1 is greater than or less than the delta pacing rate from sensor number 2 determines if equation 1 or equation 2 is implemented to determine the blend ratio used to determine the blended delta pacing rate signal.

The graph of FIG. 4 can be analyzed referring to four different time periods or intervals, namely, from when T=0 to 50, T=50 to 100, T=100 to 300, and T=300 to 350.

Referring to the time frame T=0 to 50, it can be seen that the blended delta pacing rate represented by the dashed line follows sensor number 1 until the blended delta pacing rate is 20 beats per minute, as shown in FIG. 3A, (here at $T \approx 5$) since 0% of the signal from sensor number 2 is used in equation 1 until this threshold. Above this point, the percentage of the delta pacing rate signal from sensor number 2 comprising the blended delta pacing rate is utilized at ever increasing ratios until the blended delta pacing rate is 57 beats per minute. Above 57 beats per minute, the blend ratio is a constant 27% sensor number 1 and 73% sensor number 2 (upper clip value/max delta rate=55/75=0.73).

At T=30, the delta pacing rate of sensor number 2 exceeds the delta pacing rate from sensor number 1, and thus, the second equation is now implemented, which is graphically illustrated in FIG. 3B. Now, 80% of the delta pacing rate from sensor number 2 is used with 20% of the delta pacing rate from sensor number 1 to define the blended delta pacing rate. Thus, the blended delta pacing rate, represented by the dashed line, closely follows the delta pacing rate from sensor number 2. Note that this response feature allows sensor number 2 to remain off until the delta pacing rate, provided by control logic 14 to blending logic 12 via line 19, exceeds 20 beats per minute. Also note that the blended response follows the fast sensor initially, sensor number 1, and smoothly migrates to the second sensor. This is a very desirable response when the initial output of the first sensor follows metabolic need but the second sensor lags metabolic need, i.e., acceleration and minute ventilation, respectively.

Referring now to interval T=50 to 100, the delta pacing rate of sensor number 2 is greater than the delta pacing rate of sensor number 1. In view of FIG. 3B, the blended response follows a constant blend of 20% sensor number 1 plus 80% sensor number 2 until the delta pacing rate (as provided by control logic 14 to blending logic 12) drops below 17 beats per minute (here at T=55). Then, the blend ratio smoothly changes to 7% sensor number 1 and 93% sensor number 2 until the delta pacing rate is 16 beats per minute. This is an example of rapid transitioning between two different blending ratios. Note that by keeping the blend mostly based on sensor number 2, the effect of rapid decay of sensor number 1 used is greatly reduced, as shown by the smooth transition of the blended rate in FIG. 4. This is a very desirable feature if sensor number 1 decays too quickly, i.e., the delta pacing rate established by an accelerometer decreases quickly to zero. Again, the blended pacing rate will closely follow the delta pacing rate of sensor number 2.

Referring now to the time period T=100 to 300, note that only sensor number 1 has a non-zero output. As shown in FIG. 4, the blended delta pacing rate initially follows the delta pacing rate of sensor number 1. However, since the delta pacing rate of sensor number 2 did not also increase, the blended response returns to zero, starting at T=110. This zero output is not represented in FIG. 4 as the time interval was not extended long enough. This blended response is very desirable if the output of sensor number 1 represents a non-physiological response. This is an example of a qualifying blending option. This qualifying is achieved by conditioning the output of sensor number 1, such as by filter 26 either in hardware or software and shown in block diagram of FIG. 2.

Referring now to time interval T=300 to 350, here, sensor number 1 has a zero delta pacing rate output, but sensor number 2 has a non-zero delta pacing rate output. Since the output of sensor number is presumed valid and is not conditioned as is sensor number 1 by filter 26, the blended response must follow sensor number 2 according to the second equation and as shown in FIG. 3B. As shown in FIG. 4 the blended response does follow the delta pacing rate output of sensor number 2, but at a somewhat reduced magnitude. Referring to the graphical representation of equation number 2 in FIG. 3B this slight reduction in magnitude is expected since at least a part of the blended output is always due to the first sensor output, comprising between 7 and 20%, depending on the delta pacing rate.

Thus, this invention provides a flexible and programmable method for various blending methods. It can also provide an intuitive method for programming and observing the blending characteristics. Proper selection of the blending characteristics can also result in a significant power savings.

Figure 5:
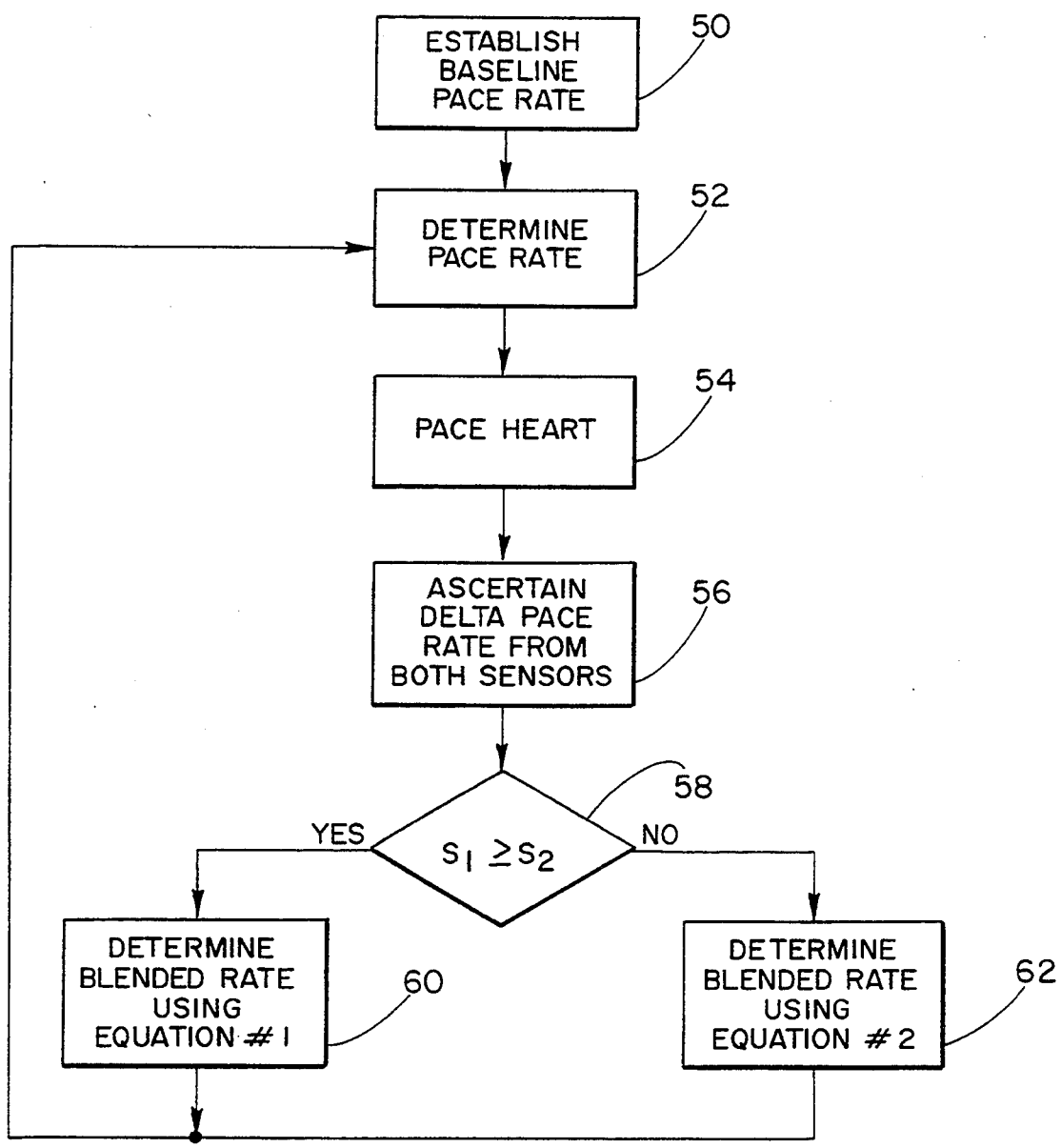
FIG. 5 is a flow diagram of the present invention including feedback illustrating how the blending ratio of the sensor outputs used to establish a single delta pace rate is determined as a function of the delta pace rate.

Referring now to FIG. 5, the algorithm implemented by blending logic circuit 12 and control logic circuit 14 shown in FIG. 2 is illustrated. Control logic circuit 14 always remains the primary control circuit controlling pace circuit 30 as a function of sensing circuit 32, which arrangement is well known in the art. In the present invention, control logic circuit 14 controls pacing circuit 30 as a function of the blended delta pace rate signal from blending logic circuit 12, rather than as a function of several delta rate pacing signals from a plurality of sensors. Thus, control logic circuit 14 operates in response to a single delta rate pacing signal defined as a function of the blending logic equations in combination with a plurality of sensor inputs. Unique to this invention is that the equations stored in blending logic circuit 12 provide a single blended delta pacing rate signal as a function of the delta pacing rate, provided by feedback line 19, which is defined each intrinsic or cardiac cycle. With this feedback, the implementation of the several sensors 20 is better suited to a particular patient's needs since the same type of sensors can be used in each patient, but the parameters stored in blending logic circuit 12 can be custom programmed.

Referring to FIG. 5 in view of FIG. 2, control logic circuit 14 first establishes a base line pace rate at step 50, such as 60 beats per minute. Next, at step 52 control logic circuit 14 determines a pacing rate as a function of the blended delta pace rate, which is determined by blending logic circuit 12 from a previous iteration of this control loop, which is established at zero during the first iteration. Control logic circuit 14 determines the pace rate as a function of the output from sense circuit 32 as well. The process of determining a pace rate as a function of sensing circuit 32, a delta pacing rate from one or more sensors, and other control algorithms such as rate smoothing, reaction recovery time, etc. is well known in the art. However, determining a pacing rate based on a blended delta pace rate from a blending logic circuit 12, which implements one or more equations and provides a delta pace rate as a function of the pace rate from a previous iteration, is new and the subject of the present invention.

After determining the delta pace rate in step 52, control logic circuit 14 instructs pacing circuit 30 to pace the heart with a pacing pulse as a function of the pace rate. After pacing the heart at step 54, control logic circuit 14 instructs blending logic circuit 12 to ascertain the delta pace rate signals from both sensors 20. It is noted if more than two sensors are implemented by pacemaker 10, the delta pace rate signals from these sensors would be ascertained at step 56 as well.

Next, at step 58, blending logic circuit 12 determines which blending logic equation is to be implemented, either equation 1 or 2, based on whether the delta pace rate signal from sensor number 1 is greater than or equal to, or less than the delta pace rate signal from sensor number 2. If the delta pace rate signal from sensor number 1 ($s_1$) is greater than or equal to the delta pace rate signal from sensor number 2, equation number 1 is implemented. Conversely, if the delta pace rate signal from sensor number 2 ($s_2$) is greater than the delta pace rate signal from sensor number 1 ($s_1$), equation number 2 is to be implemented.

Next, at steps 60 and 62, blending logic circuit 12 then determines the blended delta pace rate signal, and communicates this blended signal to control logic circuit 14 via line 60. (See FIG. 2). This blended delta pace rate signal is determined by blending logic circuit 12 by the appropriate equation at step 58 based on the delta pace rate established by the previous cardiac cycle, as provided by control logic circuit 14 via line 19, and as a function of the delta pace rate signals provided by sensors number 1 and 2. Referring again to FIGS. 3A and 3B, the percentage of the delta pace rate signal from sensor number 2 is ascertained, wherein the difference from 100% is the percentage of the delta pace rate signal from sensor number 1 that is implemented. Upon determining the blended delta pace rate at steps 60 or 62 using the appropriate equation, this blended signal is then communicated to control logic circuit 14, and will be utilized at step 52 during the next iteration.

The blended delta pace rate is determined whenever new data is available from one or more sensors. Since sensor data is normally averaged, new blended delta pace rates may be processed at a rate less than, equal, or greater than the cardiac cycle. Control logic circuit 14 uses the most recently determined blended delta pace rate signals. Thus, during subsequent iterations, control logic circuit 14 will instruct pace circuit 30 to pace the heart as a function of one or more blended delta pace rate signals which were generated between pace pulses. Other techniques for processing the blended delta pace rate signal from blending logic circuit 12 can be performed as well, and limitation to using one or averaging the blended delta pace rate signals is not to be inferred. Again, in the preferred embodiment, it is only necessary that a blended delta pace rate signal be available once per iteration.

Referring back to FIG. 2, external programmer 16 is provided with a graphics interface such that the equations programmed into blending logic circuit 12 can be graphically illustrated to the programmer. Programmer 16 has a display, such as an LCD display, which graphically illustrates FIGS. 3A and 3B, which correspond to equations one and two programmed into blending logic circuit 12. The software incorporated into the external programmer 16 includes a routine which allows experimentation such that the physician can input a variety of scenarios of hypothetical sensor outputs from sensors 1 and 2. The equations will then be executed in software based on these inputs and the blended outputs graphically illustrated, such as in FIG. 4. Thus, the physician can ascertain whether or not the blended response curve to the sensor input signals is acceptable before programming the equations into the blending logic circuit 12. Thus, equations one and two, as graphically represented in FIGS. 3A and 3B, can be executed based on a variety of input scenarios to see if the blended response is acceptable before finally downloading the equations into blending logic circuit 12.

In summary, rate adaptive blending of a plurality of sensor signals is achieved by the present invention. Only a single delta pacing rate signal is provided to control logic 14 since blending logic circuit 12 dynamically blends the delta pacing rate signals from two sensors or more sensors as a function of the pacing rate. It is recognized more complex equations can be programmed into microprocessor-based blending logic circuit 12 to blend signals from two or more sensors, and limitation to blending sensor outputs from only two sensors is not to be inferred. The present invention provides for a choice of fundamentally different blending options by programming via telemetry. Further, this blending technique allows for responding to both physiological and non-physiological sensor inputs, and power reduction is achieved by rate dependent activation of the second sensor.

The graphical user interface of the external programmer allows the physician to observe the blending characteristics while defining the parameters for the equations. While a variety of blending equations can be provided, one key feature of the present invention is blending signals from two or more sensors, rather than simply using one to the exclusion of the others. Further, the blending ratio is dynamically changing depending on the delta pacing rate and based on the magnitude of a signal from one sensor in reference to the others. In the preferred embodiment, these equations are stored in memory and executed by the microprocessor-based blending logic circuit 12, however, these equations can be implemented using analog techniques as well by using comparators, integrators, differentiators and the like. The digital embodiment is the preferred invention in that it can be quickly and easily programmed and implemented in hardware.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself. For instance, it is to be recognized that entirely new equations could be programmed into blending logic circuit 12 with programmable parameters as well. And thus, limitation to a fixed set of equations with programmable parameters is not to be inferred.

We claim:

1. A cardiac pacemaker, comprising;
   (a) pacing means for pacing a patient's heart as a function of a pacing signal at a pacing rate;
   (b) first and second sensing means for sensing attributes of a patient's body and generating a first and second output, respectively, indicative of said respective attributes;
   (c) blending logic means coupled to said first and second sensing means and said pacing means for blending said first and second outputs as a function of the pacing rate serving as feedback and generating a delta pacing rate signal, said delta pacing rate signal comprised of a first percentage of said first sensing means output and a second percentage of said second sensing means output, said blending logic means including memory means storing an equation defining said first and second percentages; and
   (d) processing means responsively coupled to said blending logic means for producing the pacing signal at the pacing rate as a function of the delta pacing rate signal.

2. The cardiac pacemaker as specified in claim 1 wherein the pacing means pacing rate at which said pacing means paces the heart comprises a base rate and a delta pace rate, and said blending logic means equation blends the first and second outputs as a function of said delta pace rate.

3. The pacemaker as specified in claim 1 wherein said equation of said blending logic means is further characterized as defining said first and second percentages as a function of said first sensing means output in view of said second sensing means output.

4. The pacemaker as specified in claim 1 wherein said first and second sensing means are each sensors providing said respective outputs which are indicative of a suggested change of the pacing rate.

5. The pacemaker as specified in claim 1 further comprising:
   (e) receiver means coupled to said blending logic means for receiving and relaying a programming signal generated external of said pacemaker, and said blending logic means further comprises means responsive to said relayed programming signal for defining said equation of said blending logic means.

6. The pacemaker as specified in claim 5 further comprising:
   (f) programming means externally coupled to said pacemaker for generating said programming signal.

7. The pacemaker as specified in claim 1 wherein said equation is a mathematical equation of at least of a second order.

8. The pacemaker as specified in claim 1 wherein said blending logic means further comprises means for electronically conditioning said first sensing means output before generating said delta pacing rate signal.

* * * * *